United States Patent [19]
Cornuejols

[11] Patent Number: 5,990,468
[45] Date of Patent: Nov. 23, 1999

[54] DEVICE FOR THE AUTOMATIC DETECTION AND INSPECTION OF DEFECTS ON A RUNNING WEB, SUCH AS A TEXTILE FABRIC

[76] Inventor: Georges Cornuejols, 7, rue du Colonel Moll, 75017 Paris, France

[21] Appl. No.: 08/836,280

[22] PCT Filed: Nov. 2, 1995

[86] PCT No.: PCT/FR95/01444

§ 371 Date: May 2, 1997

§ 102(e) Date: May 2, 1997

[87] PCT Pub. No.: WO96/14460

PCT Pub. Date: May 17, 1996

[30] Foreign Application Priority Data

Nov. 2, 1994 [FR] France .................................... 94 13419

[51] Int. Cl.$^6$ .............................. D06H 3/08; G01N 21/89
[52] U.S. Cl. ................................ 250/208.1; 250/559.05; 250/559.08; 250/559.46; 348/88; 348/128; 356/430
[58] Field of Search ........................... 250/208.1, 559.04, 250/559.05, 559.07, 559.08, 559.4, 559.42, 559.43, 559.44, 559.45, 559.46; 348/88, 128; 356/429, 430

[56] References Cited

U.S. PATENT DOCUMENTS 4,748,334  5/1988  Kobayashi et al. .
5,708,470  1/1998  Holford ...................................... 348/61
5,742,398  4/1998  Laucournet ............................. 356/429

FOREIGN PATENT DOCUMENTS 0306742  3/1989  European Pat. Off. .
2701766  8/1994  France .
92/08967  5/1992  WIPO .

*Primary Examiner*—John R. Lee

[57] ABSTRACT

The device includes a motor that move the web and an electronic camera which supplies a signal representing an image of the web formed on an image sensor having photosensitive points. The device has synchronization of the duration of a predetermined number of successive pitches of the web passing through the optical field of the camera and the duration separating the start of two successive imaging operations of the camera. Thus, an optical filtering is performed. From one image to the next, the same photosensitive point of the sensor corresponds to identical portions of threads and interstices of the web, so that any optical variation of the threads or interstice is detected. The signals representing the images produced by each photosensitive point during successive shots correspond to zones of material with similar designs. If there is no difference in the material between two successive zones observed in this manner, and in particular if there is no defect, the representative signals corresponding to these zones are exactly identical. The processing of the signal is therefore simplified and makes it possible to detect defects of very small size and/or very little different from the normal pattern.

20 Claims, 3 Drawing Sheets

DEVICE FOR THE AUTOMATIC DETECTION AND INSPECTION OF DEFECTS ON A RUNNING WEB, SUCH AS A TEXTILE FABRIC

BACKGROUND OF THE INVENTION

1. Field of the Invention

The present invention concerns a device for optical inspection of moving material. It applies to all materials which bear a lattice and in particular textiles, cloth, wallpaper, plastic, printed materials or dyed weaves.

2. Related Art

Inspection devices known at present have an electronic camera or an array of photosensitive components, generally linear, the optical field of which is constant, in width and time frequency of view capture.

The duration between the start of two successive view captures is therefore independent of possible changes in speed of running of the material or changes in pitch of the lattice borne by successively inspected materials. The two lattices, that of the individual inspection areas, linked to the optoelectronic system, and that of the textile, interfere and prevent any fine inspection.

This is because, on the one hand, when the textile lattice has a mesh which is smaller than that of the optoelectronic system, a defect on only one element of the textile lattice cannot be detected by the inspection system since it causes too small a variation in signal. On the other hand, when the textile lattice has a mesh which is larger than that of the optoelectronic system, the latter detects each space between the elements of the textile lattice and interprets it as a perforation in the lattice.

French patent application FR 93 02279 is known which describes a method and device for woven textile fabric image processing. Each fabric having a repetitive design and being defined by its period, the method of this document consists of acquiring an image and filtering it by subtracting, at each digital illumination value of a point of the image corresponding to a point of the fabric, the digital illumination value of another point of the image which is substantially displaced by one period of the cloth structure. This is intended to avoid the effects due to the cloth framework, that is to say the design which is periodically reproduced on the cloth, during weaving.

The filtering thus performed is purely electronic and is performed a posteriori on an image which, at view capture, has no particular characteristic apart from being in synchronised with the running of the cloth so that each view capture corresponds to the same distance travelled by the cloth.

Since the image capture performed by this camera is synchronised with the speed of running of the fabric, between two view captures, the same length of fabric is passed under the camera, whatever the speed of movement of the fabric. However, between two points of one image or between two points of two images, the number of threads or the number of lattice pitches or the number of framework periods which have passed in the camera field between two view captures is not an integer number or the inverse of an integer number, but only a constant number, unvarying with the speed of the cloth.

Thus the lattices of the points observed during view captures and that of the cloth threads have the same defect as described above: two points at which the illumination values are subtracted, since they are approximately one period apart, may correspond one to an interstice between threads and the other to the centre of a thread. The result of the difference then gives a high value even though the cloth has no weaving defect. Conversely, a defect, such as a thick thread which fills up the said interstice, may correspond to a small difference in illuminations. It is then not detected according to the method of the document. Again, the smallest defects may not be detected by this method.

Consequently, no solution is satisfactory and only a few extremely visible defects are detected by these systems, that is to say holes in the textiles and possibly strongly contrasting threads.

The present invention intends to remedy these drawbacks by synchronising the duration between two view captures of the image sensor and the duration of passage of one or more pitches of the lattice borne by the material.

SUMMARY OF THE INVENTION

To this end, the present invention proposes, according to its first aspect, a device for inspecting material having a lattice of regular pitch, including a means for moving the said material and at least one electronic camera having a photosensitive point sensor and supplying a signal representing an image formed on the said sensor, a camera in the optical field of which the said material moves in the course of inspection, characterised in that it has a synchronisation means adapted so that, in the direction of running of the material, the pitch of the material lattice is a multiple of the pitch between the areas observed by the photosensitive points of the camera, each said lattice pitch corresponding substantially to an integer number of pitches of the said observed areas.

According to a second aspect, the present invention proposes a device for inspecting material having a lattice of regular pitch, including a means for moving the said material and at least one electronic camera having a photosensitive point sensor and supplying a signal representing an image formed on the said sensor, a camera in the optical field of which the said material moves in the course of inspection, characterised in that it has a synchronisation means adapted so that, in the direction of running of the material, the pitch between the areas observed by the photosensitive points of the camera is a multiple of the pitch of the material lattice, each said pitch of the said observed areas corresponding substantially to an integer number of pitches of the said material lattice.

By virtue of these provisions, the image-representing signals originating from photosensitive points following one another in the view capture(s) correspond to areas of the material similar in their design.

If an area observed by a first photosensitive point of the camera, during a view capture, has a certain ratio of normal thread surface area over the total surface area of the area observed, and therefore another ratio of interstice surface area over the said total surface area, the second point, the illumination value of which will be compared to the illumination value of the first point, has the same ratios.

If the material has no difference between the two successive areas which are observed in this way, and in particular, no defect, the image-representing signal is identical. The processing of this signal is therefore simplified and makes it possible to detect defects of very small dimensional significance and/or of very low contrast with the normal design.

According to a particular embodiment, the material is a woven textile, each lattice pitch of which has a predetermined number of threads perpendicular to the direction of running in the camera field and in that each lattice pitch corresponds to the said predetermined number of pitches of the areas observed by the photosensitive points of the camera.

By virtue of these provisions, the invention applies to woven materials, and in particular woven textiles.

According to another embodiment, the device according to the present invention has a means for tensioning the material which avoids folds in the direction perpendicular to the movement.

By virtue of these provisions, the material lattice is substantially constant during the whole inspection duration and/or in the entire optical field of the camera.

According to another embodiment of the invention, the synchronisation means has an encoding means mechanically linked to the said material, and it sends at least one pulse each time the material has moved forward in the camera field, by a predetermined length.

By virtue of these provisions, the speed of movement of the material is detected by the synchronization means, and the duration between two successive view captures performed by the camera is directly linked to the said movement. The inspection can then be performed with a variable speed of movement of the material, without disrupting the inspection.

In particular, by virtue of these provisions, a visual inspection by an operator can be carried out in parallel with the inspection performed by the camera, the operator directly controlling the instantaneous inspection speed. Still more particularly, the inspection performed by the camera can assist the operator in his visual inspection.

According to a still more particular embodiment, the synchronisation means has a division means which receives the successive pulses coming from the encoding means and sends a pulse each time that the encoding means has sent a predetermined number of successive pulses.

By virtue of these provisions, knowledge of the number of lattice pitches per unit length in the direction of running makes it possible to perform the synchronisation directly by dividing the said unit length, which is represented by the pulses coming from the encoding means, by the said number, the passage of one lattice pitch, possibly multiplied subsequently, thus corresponding to the command for start of view capture by the camera.

According to another embodiment, the synchronisation means has an optical sensor, in the optical field of which the material passes in the course of inspection, an optical sensor which sends a signal representing the speed of movement of the material.

By virtue of these provisions, an optical sensor can send a substantially periodic signal when the speed of movement of the material is substantially constant, the period of this signal being inversely proportional to the speed of movement of the material.

According to a still more particular embodiment, the phase of the signal coming from the optical sensor is automatically controlled by an automatic control means.

By virtue of these provisions, possible local irregularities of the lattice in front of the optical sensor are eliminated by the use of this automatic control means.

According to another embodiment, the device according to the present invention has a vertical differentiation means which receives the image-representing signals coming from the electronic camera and sends a signal representing the difference, for each photosensitive point of the camera, of the image-representing signals originating successively from the said point.

By virtue of these provisions, the defects appear in the said difference-representing signal and a simple detection of threshold crossing makes it possible to detect them.

According to one application of the present invention, the pitch of the material is the pitch of a lattice of coating points. The invention therefore applies particularly to materials, in particular textiles, which are coated.

According to another application of the present invention, the pitch of the material is the pitch of a design made in relief by embossing or graining of the said material or by weaving of threads composing the said material. The invention therefore applies particularly to materials embossed or grained by a cylinder with repetitive designs of small size in the direction of running. It also applies to cloths having a weaving relief.

According to another application, the pitch of the material is the pitch of a coloured design resulting from weaving of the said material or printing on the said material.

The invention therefore applies particularly to textiles, paper and other materials coloured by printing or weaving of threads of different colours.

According to another embodiment, the device according to the present invention has a means for automatically controlling the view capture duration of the electronic camera with the luminous intensity received by the electronic camera sensor which receives the image-representing signal coming from the electronic camera and supplies to the said electronic camera a view capture duration control signal.

By virtue of these provisions, materials of different transparencies and/or different transmittance may be inspected without any manual adjustment being necessary.

According to another embodiment, the device according to the present invention has at least one means for adjusting the size of the optical field of the camera.

By virtue of these provisions, the pitch of the lattice of areas each inspected by one photosensitive point of the camera, in the direction perpendicular to the direction of movement, can also be a multiple of the pitch of the material lattice. Inspection of the material can then also be made by differentiation between signals coming from photosensitive points next to one another laterally.

According to another embodiment, the device according to the present invention has a row of light sources controlled by an inspection computer in order to be lit individually or by group taking into account the passage of detected defects.

By virtue of these provisions, an operator can display the detected defects and assign a treatment to them, for example, validating or de-validating their detection, recording their image or position, ordering a treatment of the material in order to eliminate each defect, etc.

By virtue of these provisions, the inspection by camera can be supplemented by an inspection by a human operator with the aim of speeding up the said inspection and making it more reliable, while maintaining the subjective elements of assessment, which depend, for example, on the constraints of the user of the material or the type of defect detected, with a view to cleaning, for example.

BRIEF DESCRIPTION OF THE DRAWINGS

The following description, given with reference to the accompanying drawings with an explanatory and in no way limitative aim, makes it possible to better understand the advantages, aims and characteristics of the present invention.

DETAILED DESCRIPTION OF THE PREFERRED EMBODIMENTS

The description of at least one preferential embodiment which follows is given, considering that the material inspected is cloth, with an aim of explaining and illustrating the invention. For persons skilled in the art of inspection by camera, the necessary adaptations of this preferential embodiment are made without difficulty, considering on the one hand the optical and geometric characteristics of the material to be inspected and on the other hand the optical and geometric characteristics of the defects to be looked for.

Figure 1A:
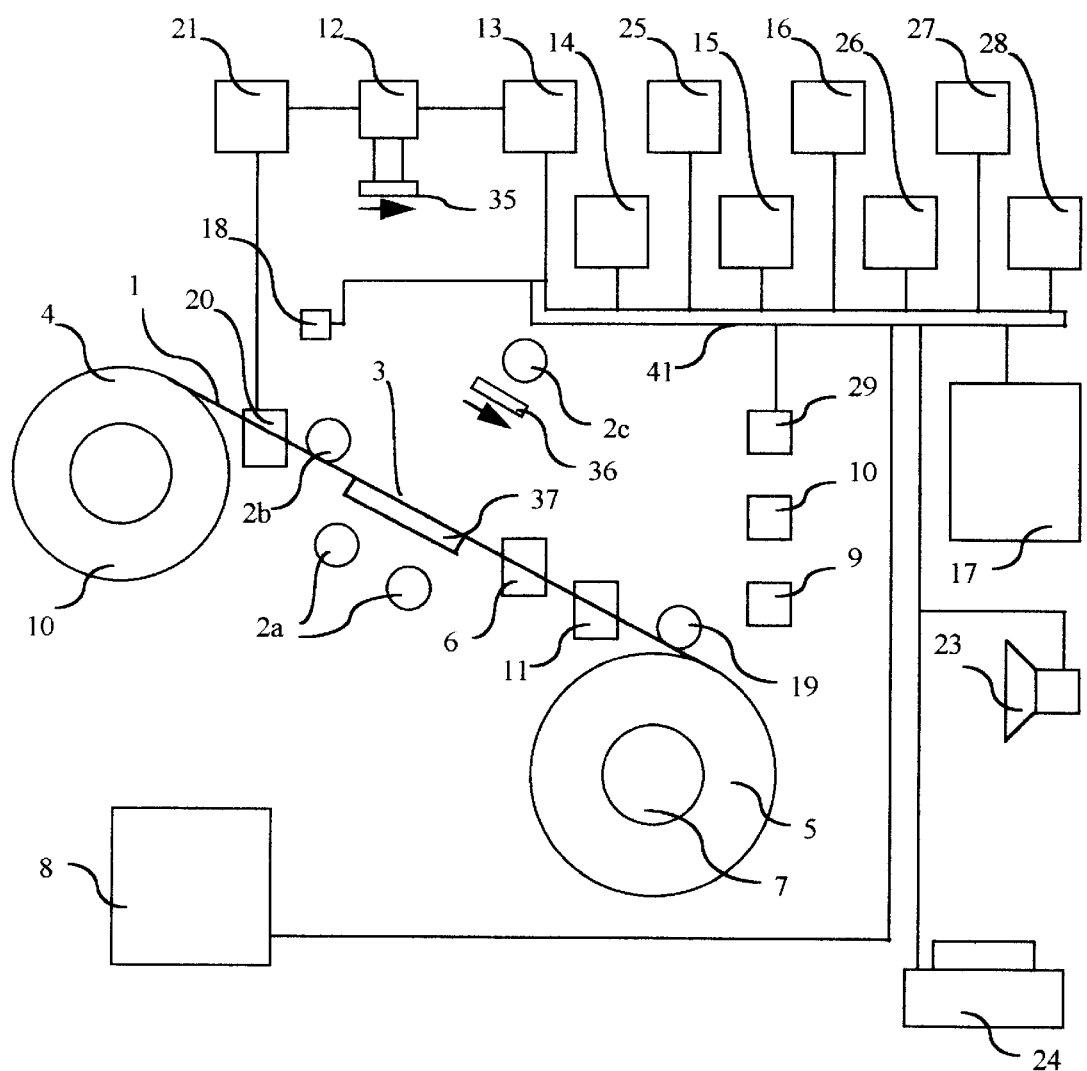
FIG. 1a depicts a block diagram of a first preferential embodiment of the device according to the present invention.

FIG. 1a depicts an inspection table 1 having lower light sources 2a, a low-angled upper light source 2b and a head-on light source 2c provided with a filter 36, a textile passage 3, an unwinder 4, a winder 5, a cut mark placer 6, a motor 7, a storage computer 8, a motor control 9, a brake 10 and a guillotine 11. Over this inspection table 1, a camera 12 having a filter 35 are arranged. Connected to the camera 12 there is a digitizer 13 which is connected, by means of a bus 41, to the storage computer 8, a vertical differentiation means 14, a horizontal addition means 25, a threshold circuit 15, a fringe extractor 16, a horizontal differentiation means 26, a vertical addition means 27, a threshold circuit 28, an inspection computer 17, a row of light sources 1, a sound emitter 23, a printer 24 and a validation means 29. Finally, an encoder 19, a frequency detection means 20 having an optical sensor and an automatic phase control means and a view capture control means 21 are depicted.

The inspection table 1 is of known type. It allows running of cloth in front of the eyes of a user, the said cloth being illuminated by at least one light source. The light sources 2a, 2b and 2c are continuous or high-frequency light sources, that is to say ones of which the light emission periods follow one another with a frequency very much higher than that of the camera 12. By way of example, a frequency of 30 kHz allows the capture of a thousand images per second by the camera 12, each image corresponding to about thirty flashes emitted by the light source operating at that frequency. It should be noted that this light source is modified compared to that which is traditionally found on inspection tables, for which the operating frequencies are of the order of a few tens or a few hundreds of hertz, frequencies adapted to the retinal persistence period.

According to the type of material which is being inspected and according to the type of defect which is being looked for, the inspection computer jointly controls the levels of the light intensities continuously emitted simultaneously by the lower light sources 2a, which are located below the inspection table and which illuminate the cloth by transparency, by the low-angled upper light source 2b, which illuminates the cloth at an incidence which is oblique and preferentially close to a right angle, and by the head-on upper light source 2c which illuminates the cloth at an angle of incidence close to the view capture angle used by the camera 12. The head-on upper light source is provided with a polarizing filter 36. The camera 12 is provided with a polarizing filter 35, the polarization axis of which is, according to the types of material and the types of defect looked for, either parallel (for example in order to detect shortages of coating points on coated cloths), or perpendicular (in order to detect marks on a reflective, for example metallic, material), to the axis of the polarizing filter 36.

The textile passage 3 is an area where the textiles run between the light source 2 and the camera 12, on the one hand, and the eyes of a user, on the other hand.

In the area of the textile passage, a cloth tensioning means 37 is located. In the example depicted, the cloth tensioning means is composed of assemblies of cones between which the cloth is gripped and which are driven in rotation by the cloth itself, around an axis which is oblique with respect to the direction of movement of the cloth. This tensioning means is well known to persons skilled in the art of equipment for the textile. industry.

The unwinder 4 is composed of an axis of rotation, around which turns a roller over which the textile unwinds, and a brake 10 which slows down the rotation of this roller. The winder 5 is composed of an axis of rotation, around which turns a roller onto which the textile winds, and a motor 7.

The cut mark placer 6 is of known type. It places, on one edge of the cloth, marks composed either of a sticker, or a clip, or a thread running through the cloth, opposite the defects detected by the device and confirmed by the user, as described below. These marks, also called cut marks in the textile industry, may have differences, for example of colour, in order to indicate different types of defect, different repetitions of defects or even different origins of defects.

The motor 7 is of known type. It activates the winder 5 in order to wind the textile on. It is controlled by the motor control 9.

The storage computer 8 is a computer of known type which stores on the one hand the positions and on the other hand the types of defects encountered on the textile. The positions are given by the encoder 19 and by the inspection computer 17 according to techniques known in the textile inspection field. The types of defect are given by the inspection computer 17, as described below.

The motor control 9 and the brake 10 are placed in order to be manipulated easily either with the foot, or with the hand, or by a production control system.

The guillotine 11 is placed on the textile passage 3 between the light source 2 and the winder 5. It makes it possible to cut the textile over its entire width in order to produce lengths of cloth, at the request of the user of this cloth.

All these first elements are of known type but are possibly connected electrically to the elements of FIG. 1 described below in order to exchange data with them.

The camera 12 is of known type. It has either a matrix image sensor, which simultaneously captures illuminations on a number of lines of photosensitive points of the image sensor and supplies a signal representing illuminations received by the said photosensitive points, or a linear image sensor which simultaneously captures the illuminations on a single line of photosensitive points of the sensor, points which follow one another in a straight line. The camera 12 supplies an electrical signal representing illuminations which arrive at each of the photosensitive points of its electronic sensor.

The digitizer 13 receives the illumination-representing signal coming from the camera 12 and supplies a digital signal representing the said illuminations.

The vertical differentiation means 14 compares, by subtraction, the digital values of the illumination-representing signals originating from the same photosensitive point of the image sensor, between two successive view captures.

The vertical differentiation means 14 thus receives the image-representing signals coming from the electronic camera and sends a signal representing the difference, for each photosensitive point of the camera, of the image-representing signals originating successively from the said point.

These illumination-representing signals are supplied by the digitizer 13. The vertical differentiation means 14 supplies a signal representing this difference. It is of known type, being composed for example of either a correspondence table or a comparator. Preferentially, it adds a constant value to the said difference so that all the values obtained remain positive.

The horizontal addition means 25 adds the successive differences coming from the vertical differentiation means 14. The number of differences added is one, two or a number of units and is supplied by the inspection computer 17.

The threshold circuit 15 sends threshold-crossing signals for the values coming from the horizontal addition means 25 which exceed, plus or minus, values supplied by the inspection computer 17. It is of known type, being composed of either a correspondence table or a set of comparators.

The fringe extractor 16 separates the threshold-exceeding signals for the points near the edges of the textile, at a distance less than a value given by the inspection computer 17. The fringe extractor applies, to the signals coming from the camera image sensor photosensitive points which receive an image from these fringes, particular processing in order to detect therein specific cloth edge defects, for example total cloth width deficiency, or excessive fringe width, detected by threshold crossings and counting of photosensitive points corresponding respectively to the cloth and the fringes, the representative signals of which are at predetermined digital values, according to techniques known to persons skilled in the art of inspection by camera.

The horizontal differentiation means 26 compares, by subtraction, the digital values of successive points of each line of illumination values on the line of the image sensor, values supplied by the digitizer 13. It supplies a signal representing this difference. It is of known type, being composed for example of either a correspondence table or a comparator.

The vertical addition means 27 adds the successive differences coming from the horizontal differentiation means 26, for each image sensor point. The differences added therefore always correspond to the same pair of photosensitive points of the image sensor. The number of differences added is one, two or a number of units and is supplied by the inspection computer 17.

The threshold circuit 28 sends threshold-crossing signals for the values coming from the vertical addition means 27 which exceed values supplied by the inspection computer 17. It is of known type, being composed of either a correspondence table or a set of comparators.

The inspection computer 17 receives the information coming from the threshold circuits 15 and 28, the encoder 19, the width measurement means 22 and the validation means 29, and processes it in order to supply at least one list of defects of each textile length, the said list including the positions located on the one hand in the direction of movement, also called "length", and on the other hand in the direction perpendicular to this movement, also called "width", and the types of defect. In addition it supplies a measurement of the textile width, a mean width measured over a length of a few centimetres of textile. It can supply a grading of the textile according to these values.

The inspection computer 17 transmits:

data to the row of light sources 18, the said data indicating which of these light sources 18 are to be illuminated, data for controlling the illumination levels to be supplied by each light source, data to be printed to the printer 24, data to be stored to the storage computer 8, a number of additions to be performed to the horizontal addition means 25, a number of additions to be performed to the vertical addition means 27, threshold values to the threshold circuits 15 and 28, possibly (in the case of FIG. 1*b*), to the frequency detection means 20, a number of pitches of the textile lattice per unit length in the direction of movement of the cloth.

The inspection computer 17 analyses on the one hand the illumination values as they come from the digitizer 13 in order to store the appearances of defects and on the other hand the geometries of the sets of points of the textile for which threshold crossings have been detected by the threshold circuits 15 and 28, in order to classify the defects according to these geometries, these digital illumination values, the values coming from the encoder 19, the lateral position of the said sets of points and data stored in the inspection computer 17.

The inspection computer 17 uses in particular different signal processing and image processing techniques which are already known.

The inspection computer 17 therefore allows:

either a semi-automatic inspection, indicating the defects detected and awaiting a manual validation by the operator.

or an automatic inspection, storing all detected defects after classification, with production of an inspection sheet possibly having a global notation, also sometimes called "demerit point".

or a classification of different lengths of cloth according to their defect rate per unit surface area with a view to inspection by an operator or by an automatic inspection system of the lengths considered as the most defective.

The row of light sources 18 is placed above the textile passage 3 and has light sources, the operation of which is controlled individually by the inspection computer 17. At each defect detected by the crossing of a threshold, the inspection computer 17 controls the light source(s) placed directly in proximity to the passage of the defect in order to illuminate it individually or try group taking into account the passage of detected defects.

The encoder 19 continuously supplies data from the length of textile which has already passed under the camera 12. It can be reset to zero either by the user, or by the inspection computer 17.

The frequency detection means 20 is here composed of a resonant phase-locked loop circuit which receives the signal coming from an optical sensor which observes an area of the moving material which is smaller than the pitch of the lattice on which the camera is synchronised. For example the optical sensor is a photodiode, in the optical field of which the threads of the inspected cloth or the points of a lattice of coating points run past one by one.

According to whether the textile lattice is composed of threads or points, for example coating points, the optical filters possibly placed in front of the optical sensor may vary.

The optical sensor thus sends a signal representing the speed of movement of the material by its frequency. The resonant phase-locked loop circuit constitutes an example of a means for automatically controlling the phase of the signal coming from the optical sensor.

The view capture control means 21 sends an approximately periodic signal resulting from the signal coming from the frequency detection means 20. This signal may have the same frequency as the signal coming from the frequency detection means 20 or a frequency half or double this. The signals coming from the view capture control means 21 control the triggering of view capture by ttie camera 12.

In this way, a means for synchronising the frequency of passage of successive meshes of the said lattice and the view capture frequency of the camera is constituted by the frequency detection means 20 cooperating with the view capture control means 21.

More particularly, the said synchronisation means substantially ensures equality between the duration of passage of one or more pitches of the said lattice and the duration separating the start of two successive view captures.

In the example described here, the optical design, the pitch of which is used for the said synchronisation, is composed of parallel woven threads, the pitch of the material lattice being the repetition pitch of one or more threads carrying the said design.

It should be noted that the value of the pitch of the areas observed on the textile by the photosensitive points of the image sensor of the camera 12 varies preferentially between ninety-five percent and one hundred and five percent of a multiple of the pitch of the textile lattice, in at least one direction of this lattice. This tolerance makes it possible to tolerate deformations of the textile lattice due to the flexibility of this textile.

The use of a multiple of the pitch of the textile lattice to constitute the pitch of the observation areas of the image sensor points is preferential for textiles of which the lattice is very dense, that is to say has a very small pitch, of the order of a few hundredths or tenths of a millimetre.

The sound emitter 23 is of known type and is controlled by the inspection computer 17 each time the latter sends a defect detection signal and a signal for controlling illumination of a light source of the row 18.

The printer 24 is of known type and is connected either to the inspection computer 17, or to the storage computer 8. It allows the issuing of labels, possibly with bar codes, and of inspection reports, as well as statistical data on the textile production.

The validation means 29 is placed within reach of the user and is used to validate or possibly eliminate the defects detected by the device which is the object of the present invention.

It should be noted that the storage computer 8 may be merged with the inspection computer 17.

A number of modes of operation may be used. According to a first mode of operation, only defects validated by the user are counted and stored. Each validated defect, whether or not it has been detected by the device, gives rise to the placing of a cut mark, to storage in the memories of the storage computer 8 and to the various document issues.

According to a second mode of operation, all defects detected by the device are taken into account with the exception of those which are eliminated by the user.

Figure 1B:
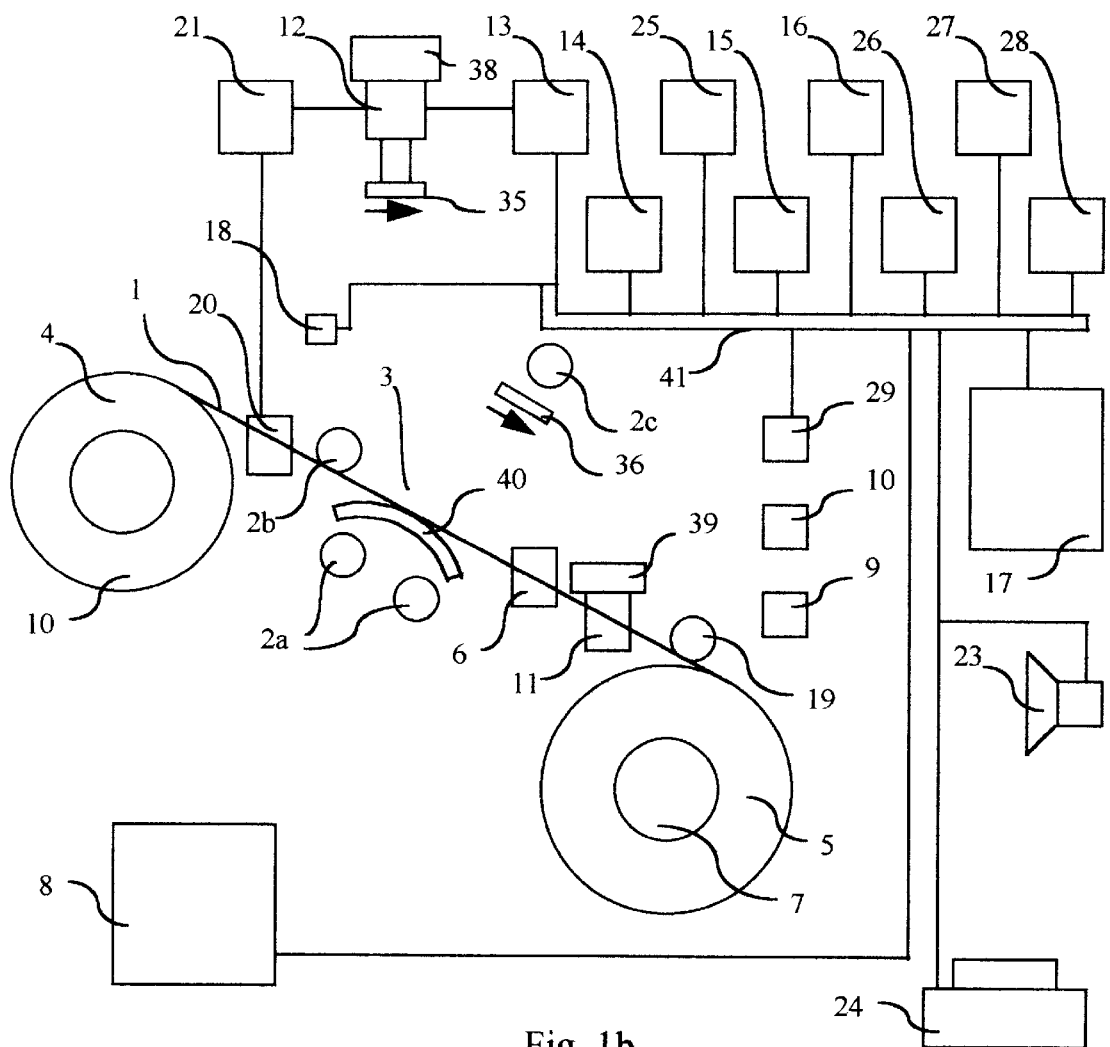
FIG. 1b depicts a block diagram of a second preferential embodiment of the device according to the present invention.

FIG. 1b depicts a second embodiment of the device which differs from the first embodiment of the device only by:

- the synchronisation means which here is composed, no longer of an optical sensor followed by an automatic phase control means, but of the encoder 19 followed by a division means 39.
- the means for tensioning the cloth by means of which the latter is drawn tight by passage over a rounded or cylindrical support 40 with a circular base, the axis of which is perpendicular to the direction of movement of the cloth.
- a view capture duration automatic control means 38 receives the image-representing signal coming from the camera and controls on the one hand the view capture duration of the camera and on the other hand the maximum speed of movement of the material, in such a way that the mean level of the image-representing signal is almost constant, and the blur, which is measured as the distance travelled by the material during view capture, is limited to a predetermined value. To this end it uses a mean value of the amplitude of the image-representing signal coming from the electronic camera, an amplitude which represents the mean luminous intensity received by the electronic camera sensor. This automatic control means uses electronic circuits and schemes known in the field of automatic lighting control for photographic films which automatically control two parameters jointly, the lens aperture and the photographing speed. Here, the lens aperture is replaced by the speed of movement of the moving material.

Figure 2:
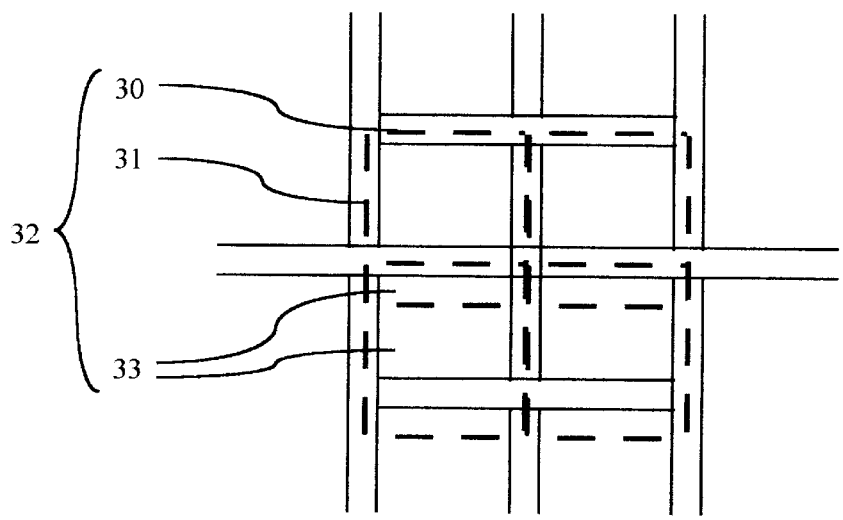
FIG. 2 depicts the lattices of a cloth and a camera.

FIG. 2 depicts the lattices of a cloth and a camera. FIG. 2 depicts horizontal threads 30 and vertical threads 31 composing the cloth 32, and rectangular areas 33 representing the view capture areas of the camera 12.

The horizontal threads 30 and vertical threads 31 are woven and have a rectangular mesh given by the weaving.

The rectangular view capture areas 33 overlap but have the same vertical pitch as that of the cloth, vertical here representing the direction of movement of the cloth. By using the system shown in FIG. 3, the rectangular areas also have the same horizontal pitch as that of the cloth 32, the direction perpendicular to the movement of the cloth. The width of the view capture areas 33 is given by the ratio of the width of the optical field of the camera 12 divided by the number of photosensitive points per line of the image sensor of the camera 12. The height of the view capture areas 33 is given by the length travelled by the textile during the duration of one view capture added to the product of the height over width ratio of each photosensitive area of the image sensor of the camera 12 and the width of the view capture area 33.

Figure 3:
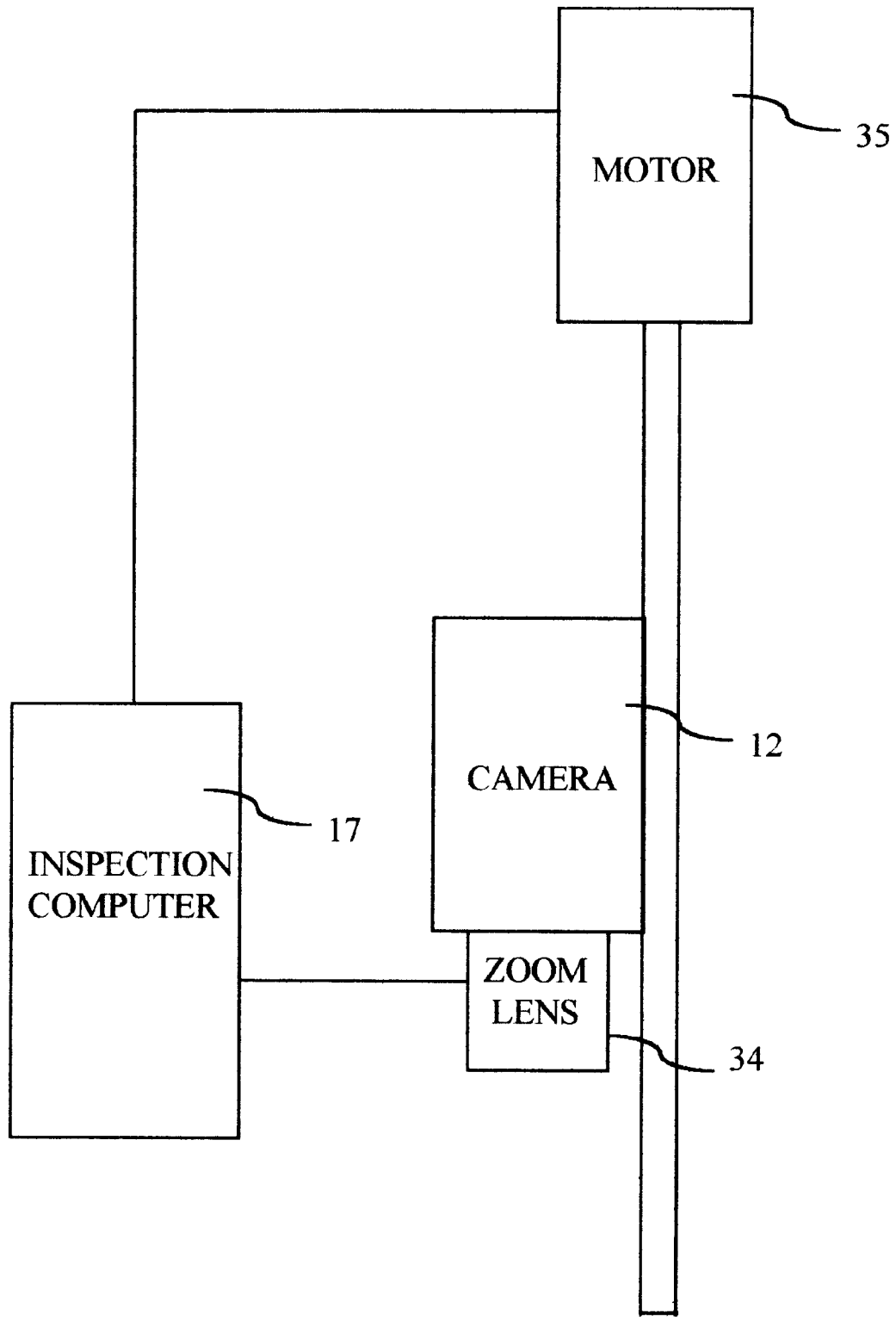
FIG. 3 depicts a second embodiment of the device according to the present invention.

FIG. 3 depicts a second embodiment of the device according to the present invention.

FIG. 3 depicts the camera 12, a zoom lens 34, a motor 35 and the inspection computer 17. The zoom lens controls the optical field width of the camera 12. The motor 35 moves the camera 12 up and down and moves it away from or closer to the textile passage 3. These two means combined make it possible to adjust the width of each view capture area 33.

The inspection computer 17 calculates, according to the signals coming from the digitizer 13, the optical field width of the camera which is substantially equal to the width of the lattice of the textile inspected. This measurement is, for example, carried out with use of Fourier transform functions. The computer 17 controls the position and operation of the motor 35 and the focal length of the zoom lens 34.

It should be understood that, according to the present invention, the view capture areas have, either automatically, or by manual adjustment assisted by the device, a lattice, the pitches of which in the lengthwise direction and widthwise direction of the textile are as close as possible to a multiple of the textile pitches. By differentiation, the device observes the smallest irregularities. By additions along the horizontal or vertical axes, detections of horizontal or vertical defects are amplified. Finally, by analysis of the data, the defects are classified.

The scope of the present invention is not limited to the embodiments described but, on the contrary, applies to the improvements and modifications within the capability of persons skilled in the art.

In particular, the pitch of the lattice of the material inspected which is used for synchronization with the duration between the starts of view captures by the camera, may just as easily be that of a relief, a woven design, a printed design, or a machined design. Thus any material undergoing treatment by a cylinder, printing or deformation, for example, has a pitch equal to the circumference of the cylinder and may be inspected by a device according to the present invention.

Furthermore, the use of other optical filters on the light sources in order to highlight particular types of defect, on particular materials, is an improvement of the present invention within the capability of persons skilled in the art, by the use of known optical techniques. A polarizing filter can, of course, be positioned both on the light source 2c and on one of the other light sources.

Finally, a number of means described above may be composed of the same processing means having at least a processor and a memory containing a program carrying out the functions described above.

NOMENCLATURE

| | |
|---|---|
| inspection table | 1 |
| light source | 2 |
| textile passage | 3 |
| unwinder | 4 |
| winder | 5 |
| cut mark placer | 6 |
| motor | 7 |
| storage computer | 8 |
| motor control | 9 |
| brake | 10 |
| guillotine | 11 |
| camera | 12 |
| digitizer | 13 |
| differentiation means | 14 |
| threshold circuit | 15 |
| fringe extracter | 16 |
| inspection computer | 17 |
| row of light sources | 18 |
| encoder | 19 |
| frequency detection means | 20 |
| view capture control means | 21 |
| sound emitter | 23 |
| printer | 24 |
| horizontal addition means | 25 |
| horizontal differentiation means | 26 |
| vertical addition means | 27 |
| threshold circuit | 28 |
| validation means | 29 |
| horizontal threads | 30 |
| vertical threads | 31 |
| cloth | 32 |
| rectangular areas | 33 |
| motor | 34 |
| zoom lens | 35 |

I claim:

1. A device for inspecting material having a lattice of regular pitch, including a motor that moves the material, at least one electronic camera having a sensor with photosensitive points and supplying a signal representing images of observed areas of the material formed on the photosensitive points, the material moving in an optical field of each electronic camera, and a synchronisation circuit synchronizing the camera and the motor so that, in the direction of running of the material, the pitch of the material lattice is a multiple of the pitch between the successive areas observed by each photosensitive point, each lattice pitch corresponding substantially to an integer number of pitches of the observed areas.

2. A device according to claim 1, wherein the material is a woven textile, each lattice pitch of which has a predetermined number of threads perpendicular to the direction of running in the camera field and in that each lattice pitch corresponds to the said predetermined number of pitches of the areas observed by the photosensitive points of the camera.

3. A device according to claim 1, wherein the synchronisation circuit is electrically connected to an encoder mechanically linked to the material, the encoder sending one pulse each time the material has moved forward in the camera field, by a predetermined length.

4. A device for inspecting material having a lattice of regular pitch, including a motor that moves the material through an optical filed of an electronic camera supplying a signal representing an image formed on a sensor after a start of imaging operations, the device further including a synchronisation circuit synchronizing a duration of passage of a predetermined number of successive pitches of the lattice of a material passing through the optical field of the camera and a duration separating the start of two successive imaging operations of the camera.

5. A device according to claim 4, wherein the synchronisation circuit is electrically connected to an encoder mechanically linked to the material, the encoder sending one pulse each time the material has moved forward in the camera field, by a predetermined length.

6. A device according to claim 5, wherein the synchronisation circuit has a division circuit that receives the successive pulses coming from the encoder and sends a pulse each time that the encoder has sent a predetermined number of successive pulses.

7. A device according to claim 4, wherein the synchronisation circuit has an optical sensor, in the optical field of which the material passes in the course of inspection, an optical sensor which sends a signal representing the speed of movement of the material.

8. A device according to claim 7, further including a phase controlling circuit for automatically controlling the phase of the signal coming from the optical sensor.

9. A device according to claim 4, further including a vertical differentiation circuit which receives the image-representing signals coming from the electronic camera and sends a signal representing the difference, for each photosensitive point of the camera, of the image-representing signals originating successively from the said point.

10. A device according to claim 4, wherein the pitch of the material lattice is the pitch of a lattice of coating points.

11. A device according to claim 4, wherein the pitch of the material lattice is the pitch of a design made in relief by embossing or graining of the said material or by weaving of threads composing the said material.

12. A device according to claim 4, wherein the pitch of the material is the pitch of a coloured design resulting from weaving of the said material or printing on the said material.

13. A device according to claim 4, further including a view controlling circuit for automatically controlling the view capture duration of the electronic camera with the luminous intensity received by the electronic camera sensor which receives the image-representing signal coming from the electronic camera and supplies to the said electronic camera a view capture duration control signal.

14. A device according to claim 4, further including at least one adjusting circuit for adjusting the size of the optical field of the camera.

15. A device according claim 4, further including a row of light sources controlled by an inspection computer in order to be lit individually or by group taking into account the passage of detected defects.

16. A device according to claim 4, wherein the material is a woven textile, each lattice pitch of which has a predetermined number of threads perpendicular to the direction of running in the camera field and in that each lattice pitch corresponds to the said predetermined number of pitches of the areas observed by the photosensitive points of the camera.

17. A device according to claim 4, further including a means for tensioning the material which avoids folds in the direction perpendicular to the movement.

18. A device according to claim 4, wherein the synchronisation circuit has an optical sensor, in the optical field of which the material passes in the course of inspection, an optical sensor which sends a signal representing the speed of movement of the material.

19. A device according to claim 18, further including a phase controlling circuit for automatically controlling the phase of the signal coming from the optical sensor.

20. A method for inspecting material having a lattice of regular pitch, including moving the material through an optical filed of an electronic camera having a photosensitive point sensor and synchronizing a duration of a predetermined number of successive pitches of the lattice of the material passing through the optical field of the camera and a duration separating the start of two successive imaging operations of the camera.

* * * * *